United States Patent [19]

Brenner et al.

[11] Patent Number: 4,859,301
[45] Date of Patent: Aug. 22, 1989

[54] SEPARATION OF ZONE FORMATION FROM ELECTROOSMOTIC IMPULSE IN TUBULAR ELECTROPHORETIC SYSTEMS

[75] Inventors: Nathaniel Brenner, Irvine; James C. Osborne, Jr., Sunnyvale, both of Calif.

[73] Assignee: Beckman Instruments, Inc., Fullerton, Calif.

[21] Appl. No.: 238,676

[22] Filed: Aug. 30, 1988

[51] Int. Cl.$^4$ .................... G01N 27/28; G01N 27/26
[52] U.S. Cl. .................. 204/180.1; 204/299 F
[58] Field of Search ............. 204/299 R, 183.3, 180.1

[56] References Cited

U.S. PATENT DOCUMENTS 4,680,201  7/1987  Hjerten .................. 204/299 R X
4,690,749  9/1987  Van Alstine et al. .......... 204/299 R Primary Examiner—John F. Niebling
Assistant Examiner—John S. Starsiak, Jr.
Attorney, Agent, or Firm—W. H. May; P. R. Harder

[57] ABSTRACT

Capillary zone electrophoresis systems are separated into two zones, one primarily for electroosmotic fow generation and the other dominated by electrophoretic effects, by the use of appropriately selected capillary materials for each region. Detection of the solute zones occurs in the electrophoretic region, minimizing or eliminating entirely the entry of the solutes into the electroosmotic region. The benefit acheived is avoidance or minimization of the adsorption of charged solutes by the capillary wall in electroosmotic flow.

16 Claims, 1 Drawing Sheet

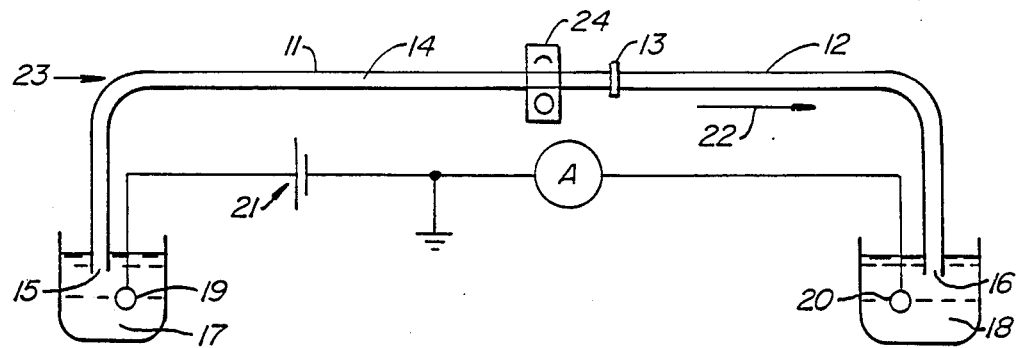
FIG._1.
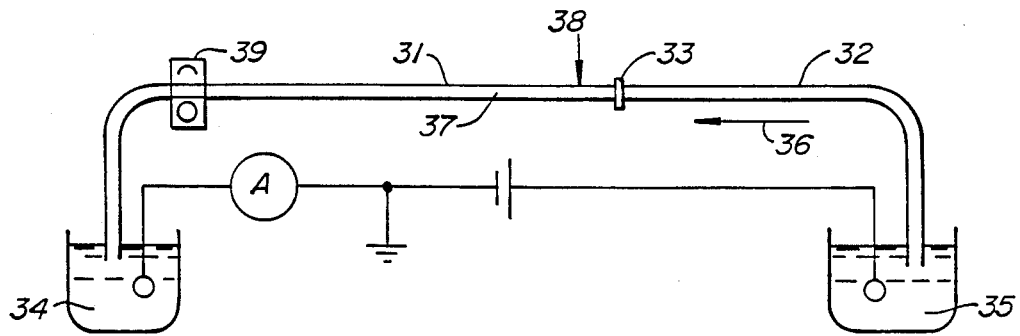
FIG._2.

SEPARATION OF ZONE FORMATION FROM ELECTROOSMOTIC IMPULSE IN TUBULAR ELECTROPHORETIC SYSTEMS

This invention relates to electrophoretic separations, and in particular to tubular electrophoresis with superimposed bulk flow driven by electroendosmosis.

BACKGROUND AND SUMMARY OF THE INVENTION

In many tubular electrophoretic systems, particularly those involving capillary tubes, a bulk flow is imposed on the solutes in addition to their electrophoretic migration. Bulk flow serves several purposes, depending on the system. In systems where the solutes include both positively charged and negatively charged species, the bulk flow assures that all solute zones move in the same direction. In some systems, bulk flow is effective in increasing the speed of the analysis and minimizing the occurrence of zone broadening. Still further, bulk flow may be used to facilitate on-column sample injection and solute detection, and further to use these features to allow for operation by automated instrumentation.

One method of achieving bulk flow is through the use of an electrokinetic potential giving rise to electroendosmosis (also referred to as electroosmotic flow). Electroosmotic flow avoids the need for pumps or external devices in general. Also, by generating the driving force directly in the tube, electroosmotic flow avoids some of the problems inherent in fluid flow transmission, such as parabolic flow profiles and other effects of interfering forces such as wall shear and dead volumes.

As is well known, electroosmotic flow is the result of a surface charge developed on the inner wall of the tubing, which draws species of the opposite charge toward the wall from the bulk fluid, leaving the core region of the bulk fluid with a net charge of the same polarity as the surface charge on the wall. This net charge responds to the electric field imposed during electrophoresis to cause the bulk flow. An unfortunate property of this surface charge on the wall, however, is its tendency to attract charged solutes in the bulk fluid and thus to cause their adsorption on the wall. This continues during the electrophoretic process, gradually lessening the magnitude of the electroosmotic force and thus the bulk flow. Band broadening is frequently a result, detracting from the sensitivity and accuracy of the analysis. In addition, the adsorption of species interferes with or prevents their detection, resulting in misleading results regarding their presence in the sample. Charged impurities may in fact not be detected at all. The adsorption is gradual and in many cases irreversible, resulting in shortened useful lives of the tubing materials as well as uncertainties and inaccuracies in the analyses.

It has now been discovered that many if not all of the detrimental effects of solute adsorption are lessened and in many cases eliminated by at least partial removal of the electroosmotic force from the portion of the system where the electrophoretic separation takes place. Thus, the separation tube is separated into two regions, one where the dominating contribution is electrophoretic separation rather than any effects of surface charges, and the other where a surface charge on the wall generates most if not all of the bulk flow for the entire system.

Expressed otherwise, the invention resides in a system where one length of tubing is inert with respect to at least a portion of the solutes in the sample (i.e., the tubing material does not interact with these solutes, either by electrostatic, affinity-based, hydrophobic or other types of interaction), and another length of tubing gives rise to sufficient electrokinetic potential to drive the bulk flow through both lengths. A detector will be arranged to detect zones formed in the separation (inert) tubing without having passed through the tubing in which the electroosmotic flow is generated.

The separation may be totally inert, i.e., inert with respect to all solutes and solvents, inert only with respect to particular solute/solvent systems, or inert with respect to only a portion of the system components with selective binding of the remainder either through affinity-based or other types of interactions. The latter type of system is useful in combining electrophoretic separations with chromatographic separations.

The two lengths of tubing are joined in fluid communicating manner so that the flow generated in the electroosmotic tubing is transmitted to the separation tubing. The relative positions of the two tubing lengths with respect to the direction of flow may vary, as may the location of sample injection point and the detector, in accordance with the system parameters. These parameters may include the types of solutes to be separated and the nature of the sample in which they are contained, as well as the type of separation desired.

Further advantages and embodiments of the invention will be apparent from the following description. Expressed in a still further manner the invention resides in the use of two lengths or regions of tubing, one having a surface charge density which is substantially greater than that of the other. The predominating effect in one will thus be the electroosmotic force, while the predominating effect in the other will be electrophoretic mobility.

BRIEF DESCRIPTION OF THE DRAWINGS

FIG. 1 is a schematic representation of one example of a separatory system in accordance with the present invention.

FIG. 2 is a schematic representation of a second example of a separatory system in accordance with the present invention.

DETAILED DESCRIPTION OF THE INVENTION AND PREFERRED EMBODIMENTS

The surface characteristics of the two regions of the system are established, at least in part, by the materials from which the tubing is made. The electroosmotic region will be made from any material which is susceptible to the formation of an electrokinetic potential and the resulting electrical double layer when placed in contact with a polar solution of an electrolyte. Silica-containing materials, notably glass, quartz and fused silica, are of particular interest, although any other materials having this property may also be used.

The configuration of the tubing is not critical and can vary widely. Electroosmotic flow can occur in tubes ranging from a few microns in diameter to several thousand. Those of most interest for purposes of the present invention will generally fall within the range of about 2 microns to about 500 microns in internal diameter.

The length of the tubing forming the electroosmotic region may likewise vary, although the magnitude of the resulting electroosmotic flow will depend at least in part on the tubing length used. For most applications, tubing ranging from about 10 mm to about 1000 mm, preferably from about 30 mm to about 300 mm, will provide the best results.

The material used for the separation region will be selected in accordance with the considerations stated above, varying depending upon the system used and the type of separations sought. For surfaces which are generally inert, polymeric materials may be used, particularly electrically inert polymeric materials. Examples are polyfluorocarbons and polyolefins. The surfaces of such inert materials may be modified in accordance with conventional techniques to impart certain interaction capabilities as desired for any particular system. Such modifications include chemical derivatizations of various kinds as well as catalytic and irradiation treatments, and coupling to proteins or other biologically active molecules, as examples.

The remainder of the system may consist of conventional elements used in electrophoretic and electroosmotic systems. These elements include electrodes, buffer solutions and voltage sources as needed to establish the electric field, detectors, both on-line and removed, sample injection ports, devices or methods, and temperature control systems. Appropriate selection of these elements will be a matter of routine choice to those skilled in the art.

Attention will now be directed to the drawings, which are offered merely as illustrative examples of systems within the scope of the invention.

FIG. 1 shows a diagram of a system for performing capillary zone electrophoresis. The system includes two lengths 11, 12 of capillary tubing. Joined at a junction 13 permitting full passage of the carrier liquid 14 for one length of tubing to the other. Of the two lengths of tubing, the first 11 is of polymeric material with an inert surface, i.e., typically one which contains little or no surface charge which might give rise to electroosmotic flow or the adsorption of charged species from the carrier liquid 14. The second length 12 is of a material susceptible to the formation of an electrokinetic potential, prime examples of which are silica and related materials. The open ends 15, 16 of the two lengths tubing are immersed in buffer solutions 17, 18 respectively, each of which contain an electrode 19, 20 across which an electric potential is imposed by a voltage source 21. In the arrangement shown in the drawing, the electroosmotic flow resulting in the electroosmotic region 12 of the tubing is in the direction of the arrow 21. The electroosmotic driving force is thus located downstream of the separation zone 11, pulling the carrier liquid 14 through the separation capillary. Injection of the sample is made at an injection point 23 at an upstream end of the separation capillary 11. As the carrier liquid 14 draws the solute through the separation capillary 11 towards the junction 13 they separate into zones due to electrophoretic separation. The zones are detected by a detector 24, in this case an on-line detector such as a direct capillary optical path detector at a wavelength such as 260 nm. The signal generated by the detector is processed in accordance with conventional means for recordation and calculation.

The embodiment shown in FIG. 2 is a variation on that shown in FIG. 1. Here, the inert capillary 31 and silica capillary 32 are arranged in the same manner as their counterparts in FIG. 1, joined by a similar type of junction 33. Also as in FIG. 1, the open ends of these capillaries are immersed in buffer solutions 34, 35, between which an electric potential is imposed. In this case, however, the electric potential is imposed in the opposite direction, resulting in electroosmotic flow in the direction of the arrow 36. As a result, the electroosmotic region 32 of the capillary system is at the upstream end, and the carrier fluid 37 flows away from the electroosmotic region rather than toward. The sample injection point 38 is moved toward the end of the separation capillary 31 which is now the upstream end, and the detector 39 is placed near where the sample injection point 23 of the FIG. 1 embodiment is located. This particular arrangement has the advantage that solutes upon separation in the separation region 31 flow directly out of the system, without passing through the electroosmotic region 32, avoiding all possibility of surface contamination of the latter.

In further variations, injection of the sample into the capillary is achieved through one end of the capillary by using a sample vessel in place of the buffer reservoir. Once the sample has entered the capillary, the sample vessel is exchanged for the buffer reservoir and separation is allowed to proceed.

The foregoing is offered primarily for purposes of illustration. It will be readily apparent to those skilled in the art that further variations, modifications and alternative arrangements are possible, still within the scope of the invention.

What is claimed is:

1. A method for detecting individual components in a sample, said method comprising:
    (a) injecting said sample into a first length of tubing which is substantially nonadsorptive with respect to at least a portion of said components, said first length being joined in fluid communication manner to a second length of tubing which is susceptible to the formation of an electrokinetic potential; and
    (b) applying an electric potential across said first and second lengths to effect electrophoretic separation of said components of said sample into zones in said first length and electroosmotic flow in said second length, said electroosmotic flow causing bulk flow in said first length driving said zones past a detector.

2. A method in accordance with claim 1 in which any electroosmotic flow generated in said first length of tubing by surface charges thereon is of substantially lesser magnitude than said bulk flow.

3. A method in accordance with claim 1 in which said first length of tubing is not susceptible to the formation of an electrokinetic potential.

4. A method in accordance with claim 1 in which said first and second lengths of tubing are capillary tubing.

5. A method in accordance with claim 1 in which step (b) comprises applying said electric potential in such a manner as to cause said bulk flow in said first length of tubing to flow toward said second length.

6. A method in accordance with claim 1 in which step (b) comprises applying said electric potential such a manner as to cause said bulk flow in said first length of tubing to flow away from said second length.

7. A method in accordance with claim 6 in which step (a) comprises injecting said sample at a point downstream of said second length of tubing.

8. A method in accordance with claim 1 in which said first length of tubing is formed of an electrically inert polymeric material, and said second length of tubing is formed of silica.

9. A method in accordance with claim 1 in which said detector is an on-line detector positioned to detect the passage of said zones past a preselected location in said first length of tubing.

10. A method in accordance with claim 1 in which said first length of tubing is substantially nonadsorptive with respect to all of said components.

11. A method in accordance with claim 1 in which said first length of tubing is substantially nonadsorptive with respect to a first portion of said components and adsorptive with respect to a second portion thereof, step (a) is performed under conditions promoting the adsorption of said first portion, and said method further comprises desorbing said first portion after step (b).

12. Apparatus for detecting individual components in a sample, said apparatus comprising:
   first and second lengths of capillary tubing joined to each other in fluid communicating manner, said second length having a surface charge density which is substantially greater than that of said first length;
   means for imposing an electric potential across said first and second lengths; and
   means for detecting chemical species moving axially inside said first length.

13. Apparatus in accordance with claim 12 in which said first length of tubing is not susceptible to the formation of an electrokinetic potential.

14. Apparatus in accordance with claim 12 in which said first and second lengths of tubing are capillary tubing.

15. Apparatus in accordance with claim 12 in which said detecting means is an on-line detector positioned on said first length of tubing.

16. Apparatus in accordance with claim 12 in which said first length of tubing is formed of an electrically inert polymeric material, and said second length of tubing is formed of silica.

* * * * *